United States Patent [19]

Schmidt

[11] 4,231,960
[45] Nov. 4, 1980

[54] PROCESS FOR THE PURIFICATION OF UREA SOLUTIONS CONTAINING BIURET AND THE LIKE

[75] Inventor: Alfred Schmidt, Vienna, Austria

[73] Assignee: OMV Aktiengesellschaft, Vienna, Austria

[21] Appl. No.: 912,328

[22] Filed: Jun. 5, 1978

[30] Foreign Application Priority Data

Jun. 8, 1977 [AT] Austria ..................... 4077/77

[51] Int. Cl.³ .......................... C07C 126/00
[52] U.S. Cl. ......................... 564/73; 208/25
[58] Field of Search .......... 208/25; 260/555 R, 555 B

[56] References Cited

U.S. PATENT DOCUMENTS

| | | | |
|---|---|---|---|
| 2,854,482 | 9/1958 | Guyer | 260/555 B |
| 3,287,407 | 11/1966 | Zardi | 260/555 B |
| 4,070,269 | 1/1978 | Reynolds | 208/25 |

FOREIGN PATENT DOCUMENTS 38-3116  4/1963  Japan ........................... 260/555 B Primary Examiner—Brian E. Hearn

[57] ABSTRACT

Disclosed is a process and apparatus for purifying and regenerating urea solutions which have been contaminated with biuret and triuret and the like during the use of the urea solutions such as in dewaxing processes. The contaminated urea solution is first contacted with ammonia in gaseous or liquid form and about one to ten percent of the ammonia is absorbed into the contaminated solution. The contaminated solution and absorbed ammonia are reacted in a reactor with heating for a period of time sufficient to complete the reaction of biuret and triuret to produce urea. The purified product solution may then be returned for further use in dewaxing processes. Excess ammonia and $CO_2$ formed during the reaction process by the decomposition of urea may optionally be separated from the purified solution and from each other with the separated excess ammonia being returned to the absorber for reuse.

3 Claims, 2 Drawing Figures

PROCESS FOR THE PURIFICATION OF UREA SOLUTIONS CONTAINING BIURET AND THE LIKE

Object of the invention is the purification of urea solutions, in particular the regeneration of aqueous urea solutions which are contaminated, for instance in the course of heating operations, due to secondary reactions or the like, by various condensation products such as biuret, triuret or the like, possibly also by cyanuric acid, ammelide or the like, but mainly by biuret. Such impurities in urea solutions are undesirable in various fields of application, such as, for instance, the production of plastic materials and artificial fertilizers and in oil refining and it is the object of the invention to provide a simple and practical process and an appropriate plant for the purification and/or regeneration of urea solutions.

Particularly large amounts of urea are used in the dewaxing of mineral oil fractions and many attempts have been made in this field for some time to reduce the losses in urea from cycling solutions for which no remedy existed up to now.

In the diesel- and middle (carbolic) oil cuts of various crude oils, paraffins are present in rather large amounts, so that the setting point of these products is comparatively high. But in order to use these fractions as diesel or lubricating oils, a much lower setting point is required, which can only be achieved by removing the paraffins. Various technical processes have been worked out to this end, an example for an important one being the urea-dewaxing process according to Edleanu.

This process is based on the fact that urea forms, with straight-chained paraffins, solid and insoluble adducts which can be separated from the remaining oil. For this purpose, the mineral oil cut is brought into contact with a concentrated aqueous urea solution (about 75 percent by weight), optionally under addition of a solvent for dilution. This results in the formation of the urea-paraffin compound described which is precipitated in solid form and may be removed by subsequent filtration. The filtrate is stripped in order to separate the solvent, the solvent is recycled and the rest is recovered in the form of a dewaxed product.

The separated solid urea-paraffin compound containing the paraffin is then cleaved under addition of water and heating, this yields pure paraffin and a urea solution which can again be used for precipitation after appropriate evaporation. This process is successfully applied in a large number of plants.

At long-term operation of such dewaxing plants, it becomes evident that—although theoretically, the urea cycle is closed,—considerable consumption, i.e. loss, of urea occurs. This is attributable in part to the technically unavoidable handling losses and the hydrolysis of the urea to ammonia and carbon dioxide and must be compensated for by the continuous addition of fresh urea.

In attempts to reduce the handling losses in urea by appropriate operational measures in order to reduce urea consumption, a further difficulty arises from a certain point on: although the plant operates normally, the setting point of the dewaxed product obtained rises continuously, i.e. the precipitating effect of the urea solution decreases. The point of turbidity of the cycling urea solution, that is the temperature at which the first solids are precipitated from the solution, sinks parallel to this at equal urea concentration by 5° to 15° C.

Investigation of this phenomenon shows that part of the urea in the urea solution circulating within the plant is converted to various condensation products such as biuret, triuret, cyanuric acid, ammelide and the like. These contaminants obviously disturb the formation of the urea-paraffin compound described above so much that removal of the paraffin is no longer possible to an adequate extent and the product obtained does not come up to requirements. In order to prevent this, it has been necessary to currently remove part of the urea cycling solution from the plant to discard it and to replace the amount discarded by fresh urea solution. This constitutes a strong detriment to the economy of the dewaxing process, since, on the one hand, it causes a continuous increase in urea consumption at long-term operation of the plant and, on the other hand, for reasons of environment protection, the urea solution removed has to be subjected to treatment in a specific processing and purification plant before it can be discharged into the draining ditch.

It was surprisingly found that a simple measure permits regeneration of the about 75 percent urea solution removed to such an extent that it is fully usable again for the sensitive urea-dewaxing plant and that the urea consumption of the process can thus be essentially lowered.

The process for the purification and regeneration of urea solutions contaminated with urea conversion products, for instance by biuret, triuret or the like, in particular for the regeneration and rendering reusable of urea cycling solutions in urea dewaxing plants, is characterized in that the urea solution to be purified, in particular a urea cycling solution or a subflow of the urea cycling solution after removal from the dewaxing process, is brought into contact with ammonia, whereby 1 to 10 percent by weight of ammonia based on the total amount of urea present are absorbed, and that this urea solution charged with ammonia is kept for a period of 30 to 240 minutes at temperatures of 110° to 170° C. in the presence of said 1 to 10 percent by weight of ammonia, and that in the case of regeneration of cycling solutions in urea dewaxing plants, the regenerated solution, optionally after separation of excess ammonia and $CO_2$, is recycled into the urea solution cycle of the dewaxing plant. Following this process, the solution, optionally after removal of ammonia and/or $CO_2$, can be directly added to the urea cycle of the dewaxing plant without further process steps, so that a product with the desired low setting point is again obtained. Ammonia can be added in the form of an aqueous solution or in the gaseous state.

It is assumed that the impurities in the urea solution disturbing the separation of the paraffins in the purification process according to the invention are partly hydrolysed, partly converted to other substances free of effects which disturb the process. This makes possible a decisive, 50 to 80 percent reduction of urea consumption or loss in dewaxing plants.

The amount of ammonia required can be adjusted by external addition of ammonia gas to the solution to be purified, for instance to the cycling solution no longer usable for dewaxing. But this also causes considerable consumption of ammonia, increasing the cost of purification or regeneration. It was found, however, that a small amount of ammonia is formed in the course of regeneration, so that all or at least part of the ammonia required for purification is formed in the regeneration or purification process itself, for instance by decomposition and hydrolysis of urea into ammonia and water. As a result, no external addition of ammonia may be required. A specific embodiment of the process according to the invention provides for the ammonia liberated in the course of purification and/or regeneration to be used for the purification and/or regeneration of the urea solution.

As the amount of ammonia liberated is only small, at least part of the ammonia remaining dissolved in the regenerated solution can be separated from the solution and recycled to the solution to be regenerated. The simplest way of separating this ammonia is by stress-relieving evaporation of the purified and/or regenerated solution, the vapors formed being fed into an absorber where they are absorbed by the incoming contaminated solutions.

Recycling of the ammonia formed in or liberated from the purified and/or regenerated urea solution in the solution to be regenerated is advantageously effected in a "one-shot" or "one-step" process combining all the steps of the process. In this case, all the process steps previously discussed are sub steps of a single process step comprising the entire purification process.

As already mentioned, the desired re-formation of urea from biuret under the effect of NH3 on the urea solution to be purified,

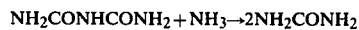

$$NH_2CONHCONH_2 + NH_3 \rightarrow 2NH_2CONH_2$$

is accompanied under the required reaction conditions by a parallel partial hydrolysis of the urea present in the solution to ammonia and carbon dioxide:

$$NH_2CONH_2 + H_2O \rightarrow 2NH_3 + CO_2.$$

The two gases formed remain in the solution, but have considerable vapor pressure.

After the reaction, the gases are removed from the urea solution and separated from one another; the ammonia is recycled to the urea solution to be purified for reaction with the biuret it contains.

According to a specific embodiment, as already mentioned, the process steps of absorption of ammonia in the contaminated urea solution resulting in saturation of the solution with ammonia, reaction of the biuret in the solution with the ammonia absorbed in the solution, removal of the ammonia and carbon dioxide from the reaction solution and separation of these two gases, are combined and carried out in one single process step.

By means of the process according to the invention, in all the embodiments described, it is easily possible to lower the biuret content of a urea cycling solution taken from a dewaxing plant from, for instance, 5 or 7 percent to 2 and, in most instances, even down to 1 percent.

A further object of the invention is a plant for carrying out the process according to the invention. The plant consists of an absorber in which the ammonia supplied through an inlet line is conveyed towards, and brought into contact with, the urea solution, in particular the cycling solution from the dewaxing plant, to be purified, in particular to be regenerated, which solution is supplied to said absorber through an inlet line by means of a pump; an, optionally heatable, reactor to which the urea solution charged with ammonia in the absorber is supplied through an outlet line, a heating means, in particular a heat exchanger and a further inlet line; from which reactor the purified, in particular regenerated, urea solution, is withdrawn, in particular recycled into the urea dewaxing plant through a line and a separator for separating the excess ammonia therefrom.

According to a specific embodiment of the plant, the outlet line for separated ammonia coming from the separator is provided to be connected to the inlet line for ammonia.

A plant proved suitable for carrying out the one-step purification and regeneration process described above is essentially characterized in that it is provided with a reactor (B1) provided with a heating means (W1), an absorber (K1) being directly superimposed on said reactor (B1), said reactor (B1) and said absorber (K1) being arranged within one common shell (M1), said absorber (K1) serving for the absorption of ammonia formed as a byproduct during treatment of the urea solution in said reactor (B1); at least one inlet line (L1, L2) with conveying pump (P1, P"), said line (L1, L2) emptying near the absorber top and serving for supplying urea solution to be purified; an outlet line (A1) starting at the top of the column and having pressure adjustment means (D) for discharging CO2 and excess ammonia; and a line (A2) for discharging the purified and regenerated urea solution, in particular for recycling of the regenerated urea cycling solution into the dewaxing plant.

BRIEF DESCRIPTION OF THE DRAWINGS

The plant and device according to the invention are explained in detail under reference to the accompanying drawings

Figure 1:
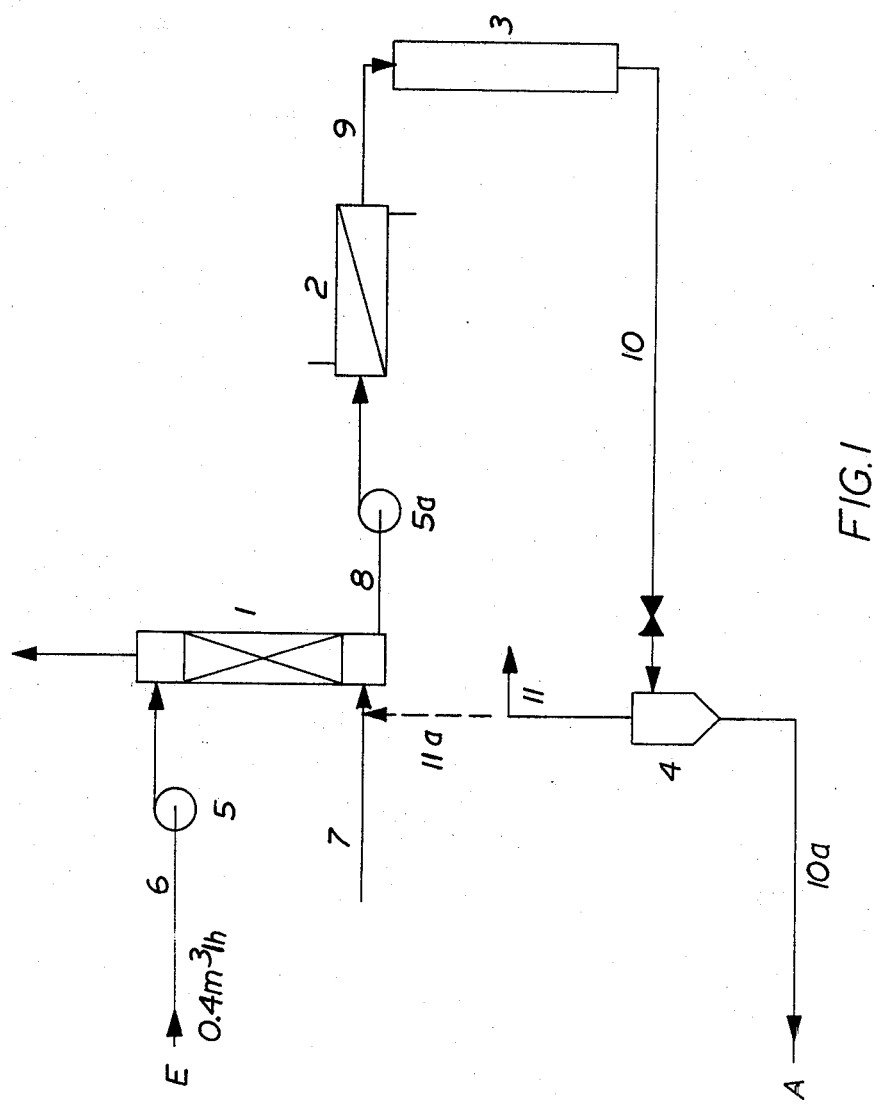
FIG. 1 shows the diagrammatic view of an embodiment according to the invention of the plant for the purification of urea in which the ammonia separated from the purified urea solution is optionally recycled into the absorber and FIG. 2 shows a preferred embodiment for carrying out the one-step purification and regeneration process.

In the plant according to FIG. 1, the urea solution E to be purified is introduced, for instance at a rate of 0.4 m³/h, at the top of the absorption column 1, the solution E for instance coming from the dewaxing plant, through line 6 by means of pump 5 which may be a piston pump or a rotary pump; then, ammonia gas charged into the absorption column 1 is conveyed towards solution E either through inlet 7 from the outside or, coming from separator 4, through recycling lines 11, 11a and inlet line 7. In column 1, the ammonia serving for the regeneration of the urea solution is absorbed by the urea solution to be purified and regenerated which is flowing downward through the column. The urea solution charged with ammonia is then fed by a pump 5a and the line 8, through the heating means, in particular the heat exchanger 2 and through line 9 into the, optionally heatable, reactor 3, in which the purification and regeneration of the urea solution is effected by reaction of the ammonia absorbed with the biuret present in the solution under appropriately adjustable pressure and temperature conditions and suitable times of direct contact of the reagents. Through line 10, the now regenerated solution is conducted to the separator 4, the CO2 and ammonia separated there is discharged to the outside through line 11, or, optionally the ammonia after separation of the CO2 is recycled into inlet line 7, and thus absorption column 1, through line 11 and line 11a shown in broken lines. The regenerated solution A is either discharged through line 10a or recycled to the dewaxing plant.

Figure 2:
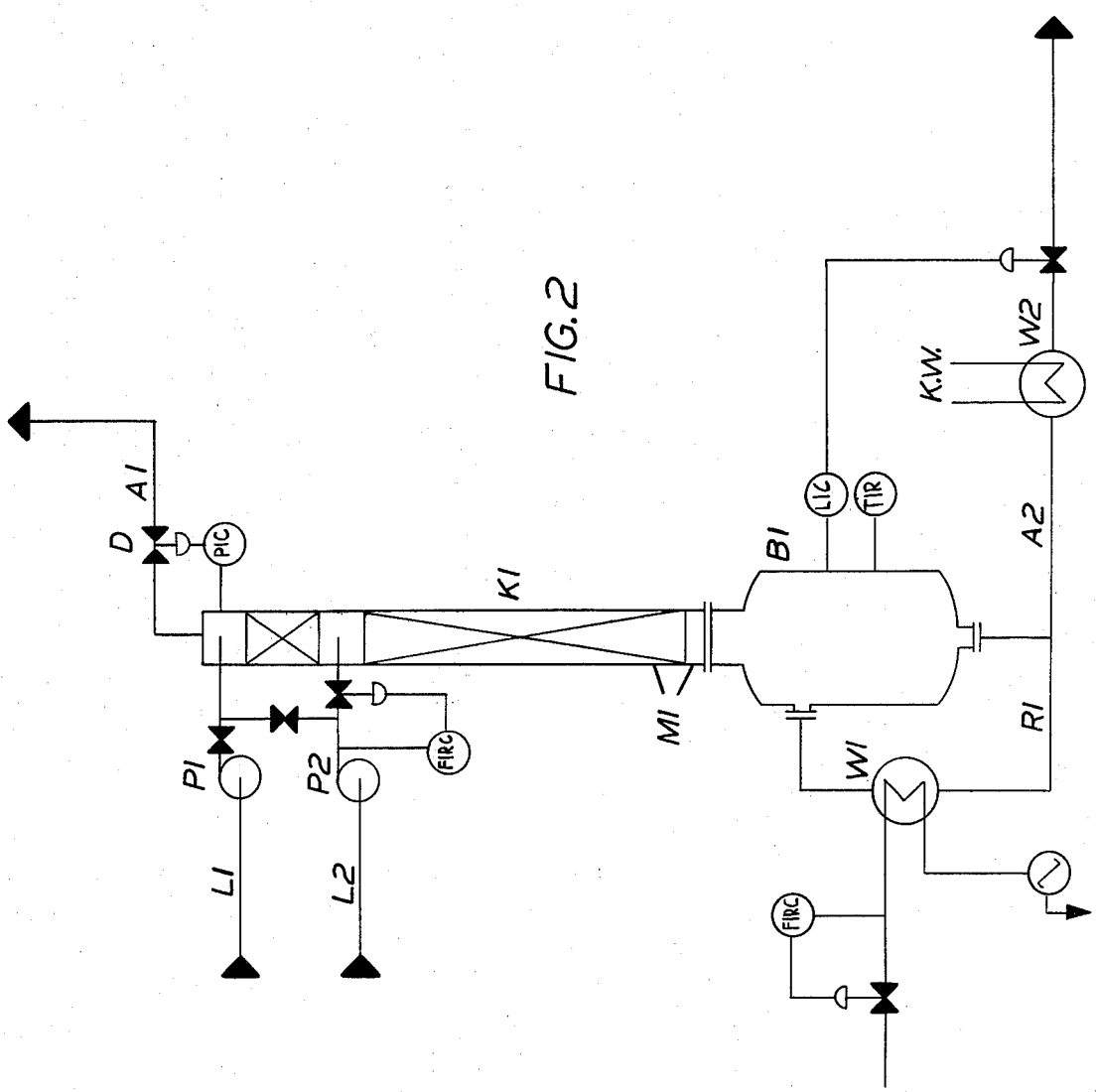

The embodiment of the plant according to FIG. 2 is particularly suitable for carrying out the one-step purification process previously described. In the plant, the absorption column 1 is directly superimposed on the reactor B1 in which the regeneration reaction takes place, within the common shell M1. The urea solution or urea cycling solution to be purified and regenerated is supplied through lines L1, L2, the amount coming into L2 being controlled by control circuit FIRC at the top of the column which is also the starting point for the discharge line A1 for carbon dioxide with pressure control means D controlled by the control organ PIC. For heating the content of the reactor or for keeping its temperature constant, the content of the reactor can be conducted via the cycling line R1 through the heat exchanger W1 and back to the reactor B1, the amount of hot medium for exchanger W1 being controlled by control circuit FIRC. Through the outlet line A2 and the cooling means, preferably the heat exchanger W2, in which cooling water CW circulates, the purified or regenerated urea solution is discharged or recycled as cycling solution into the dewaxing plant. The path of the regenerated urea solution controlled by control circuit LIC.

The process is explained in detail by means of the following practical examples:

EXAMPLE 1

A discontinuously operating reactor is charged with urea solutions each containing the amounts of urea, water and ammonia indicated in Table 1 in the form of a 33% aqueous ammonia solution. The conditions under which the regeneration is carried out, such as temperature, pressure and period of time, and the results of the tests, namely, the finally remaining residual amount of biuret in the solution, are evident from Table 1.

The following Table 2 shows the amount balance of the plant in operation, with the lines through which the corresponding amounts of material are charged or discharged bearing the same reference numerals as in FIG. 1.

TABLE 2

| Reference Number of Line in FIG. 1 | 6 | | 7 | | 8 | | 10 | |
|---|---|---|---|---|---|---|---|---|
| Amount | kg/h | % | kg/h | % | kg/h | % | kg/h | % |
| NH$_3$ | 0 | 0 | 50 | 100 | 50 | 4.75 | 104.1 | 9.9 |
| CO$_2$ | 0 | 0 | 0 | 0 | 0 | 0 | 77.4 | 7.4 |
| H$_2$O | 270 | 27 | 0 | 0 | 270 | 25.7 | 238.3 | 22.7 |
| Urea | 660 | 66 | 0 | 0 | 660 | 62.8 | 595.2 | 56.7 |
| Biuret | 70 | 7 | 0 | 0 | 70 | 6.7 | 35 | 3.3 |
| Total | 1000 | 100 | 50 | 100 | 1050 | 100 | 1050 | 100.0 |

EXAMPLE 3

In a plant according to FIG. 1 with recycling line for the ammonia from the regenerated solution into the absorber, the discharge solution from the dewaxing plant is first saturated with ammonia in the absorber and conveyed by means of a pressure pump through a heat exchanger into the reactor. The reacted solution is unstressed, whereby the major part of the dissolved ammonia is liberated and recycled to the absorber. The unstressed solution could be recycled to the solution cycle of the urea dewaxing plant without difficulty. The operating solutions and the synthetic solutions used for comparison are each of the following composition: composition of the operating solution:

| Urea | 63.4% |
|---|---|
| Biuret | 5.7% |
| Water | 30.9% |

TABLE 1

| | RESULTS OF THE PROCESS CARRIED OUT IN THE REACTOR | | | | | | | Dilution | |
|---|---|---|---|---|---|---|---|---|---|
| Test No. | Urea Content % by weight | Biuret Content % by weight | CO$_2$ Content % by weight | Time of Direct Contact h min | Reaction Pressure kp/cm$^2$ | Addition of NH$_3$ in g | Reaction Temperature °C | Starting Solution: water: in vol.parts (ml) | 33% NH$_3$ Solution |
| Vk/3 | | under 1 | 0.2 | 1 25 | 18–20 | 23.4 | 120 | 125:100:80 | |
| Vk/11 | 14.2 | under 1 | | 1 51 | 18–20 | 14.6 | 160 | 100:50:50 | |
| Vk/12 | 26.9 | under 1 | | 1 25 | 20–22 | 21.9 | 120 | 100:50:75 | |
| Vk/14 | 15.9 | under 1 | | 1 28 | 19–21 | 14.6 | 160 | 100:50:50 | |
| Vk/15 | 22.4 | under 1 | | 1 28 | 23–25 | 21.9 | 160 | 100:50:75 | |

EXAMPLE 2

In a plant according to FIG. 1 without recycling line, the process according to the invention was carried out at a temperature of 150° C. under addition of 5 percent by weight of ammonia, at a time of direct contact in the reactor of 2 hours and a pressure of 23 to 24 atü.

Composition of the synthetic solution:

| Urea | 70% |
|---|---|
| Biuret | 5% |
| Water | 25% |

The results of the tests are evident from Table 3.

TABLE 3

| | Material Balance of Reaction Tests | | | | | | | |
|---|---|---|---|---|---|---|---|---|
| Test No. | Solution | Temperature °C. | Amounts of NH$_3$ added in % b.w. | Time of Direct Contact h | Pressure (kg/cm$^2$) | Content of CO$_2$ (after test) | Amount of Urea corresp. to Formation of CO$_2$ | Urea Content after Test | Biuret Content after Test |
| A/1 | Operating | 140 | 5 | 2 | 15.5 | 7.7% | 10.5% | 64.1% | 1.3% 1.4% |

TABLE 3-continued

Material Balance of Reaction Tests

| Test No. | Solution | Temperature °C. | Amounts of NH₃ added in % b.w. | Time of Direct Contact h | Pressure (kg/cm²) | Content of $CO_2$ (after test) | Amount of Urea corresp. to Formation of $CO_2$ | Urea Content after Test | Biuret Content after Test |
|---|---|---|---|---|---|---|---|---|---|
| A/2 | Solution Operating Solution | 140 | 10 | 2 | 16.0 | 10.9% | 14.8% | 60.8% | 1.5% 1.4% |
| A/3 | Synthetic Solution | 160 | 5 | 1 | 16.2 | 23.3% | 31.7% | 53.4% | less than 1% |
| A/4 | Operating Solution | 160 | 10 | 1 | 18.5 | 21.9% | 29.8% | 49.2% | less than 1% |
| A/5 | Operating Solution | 160 | 10 | 2 | 19.0 | 20.7% | 28.2% | 48.1% | less than 1% |
| A/6 | Synthetic Solution | 140 | 5 | 1 | 15.0 | 5.1% | 6.9% | 68.9% | 1.8% 1.7% |

EXAMPLE 4

The tests were carried out in a plant as shown in the schematic representation of FIG. 2. It consisted of a heated reactor with a superimposed column. At the head (top) of the column, the urea solution was charged in amounts of 660 kg/h. The pressure in the reactor was adjusted by unstressing the gas at the top of the column in such a manner that the solution in the bottom started to boil at 150° C.; the pressure amounted to 11 at. The gas withdrawn at the top of the column consisted of pure carbon dioxide, the ammonia formed was absorbed by the urea solution flowing in. The level in the bottom of the column was kept constant by means of a drain valve; the solution withdrawn at a rate of 595 kg/h was analyzed, the results after varying times of direct contact in the reactor are evident from Table 4.

TABLE 4

| Product and time of direct contact | Urea % b.w. | Biuret % b.w. | $CO_2$ % b.w. | $NH_3$ % b.w. | Ratio Urea:Biuret |
|---|---|---|---|---|---|
| Charge Solution | 43 | 3.7 | 0 | 0 | 11.6 |
| Product 1 (4 h) | 34 | 1.4 | 1.8 | 5.6 | 24.2 |
| Product 2 (5 h) | 34 | 1.6 | 2.4 | 5.8 | 21.2 |
| Product 3 (6 h) | 33 | 1.6 | 2.3 | 6.1 | 20.6 |

It is evident from these values that the biuret values in the product solutions are correspondingly lowered. The solution contained an average of about 5.8% ammonia, the carbon dioxide content was slightly above 2%.

It is thus possible to achieve the regeneration of the solution without the addition of external ammonia.

When proceeding according to this example, the savings in urea in an industrially operated urea dewaxing plant are of the following values:

In the respective dewaxing plant, 6500 kg of urea per day had to be used up to now, with 61.8% or 4020 kg of urea or biuret contained in the discharge solution which was left unused up to now. The major part of this amount is saved by using the process according to the invention, of course after subtracting the about 1300 kg of urea hydrolyzed in the test plant. The expected saving in urea thus amounts to 4020 minus 1300 kg/day, i.e. 2720 kg/day or about 900 metric tons of urea per year.

The energy consumption amounts to about 0.33 t/h steam and about 10 kWh/h electricity. Personnel is required for occasional supervision only.

Up to now, the urea dewaxing plant discharged virtually the entire amount of urea required, i.e. 6500 kg/day, to the outside in the form of urea, biuret and ammonia, totalling about 3030 kg of nitrogen per day.

By operating the regeneration plant, this amount was reduced to about 70 percent of the amount required up to then. This means that the use of the regeneration plant according to the invention also exerts a beneficial influence on the sewage situation.

What is claimed is:

1. A process for the purification and regeneration of urea solution contaminated by urea conversion products such as biuret, triuret and the like, comprising the steps of contacting the contaminated urea solution with ammonia whereby about 1% to about 10% by weight of ammonia based on the total amount of urea is absorbed, maintaining said contaminated urea solution in contact with ammonia for a period of about 30–240 minutes at a temperature of about 110° to about 170° C. to react the conversion products with the ammonia, separating $CO_2$ and excess ammonia from said urea solution and separating said $CO_2$ and excess ammonia from each other, said steps of contacting, maintaining, separating $CO_2$ and excess ammonia from the urea solution and separating the $CO_2$ from the excess ammonia being carried out simultaneously.

2. The process as set forth in claim 1 further including the step of reusing the separated ammonia as a portion of the ammonia utilized in the step of contacting the contaminated urea solution with ammonia.

3. The process as set forth in either of claims 1 or 2 wherein said contaminated urea solutions are urea cycling solutions from a dewaxing process.

* * * * *